(12) United States Patent
Sears et al.

(10) Patent No.: US 8,012,213 B2
(45) Date of Patent: Sep. 6, 2011

(54) APPARATUS AND METHOD FOR SUPPORTING VERTEBRAL BODIES

(75) Inventors: William Sears, Killara (AU); B. Thomas Barker, Bartlett, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 12/321,186

(22) Filed: Jan. 16, 2009

(65) Prior Publication Data
US 2009/0132053 A1 May 21, 2009

Related U.S. Application Data

(63) Continuation of application No. 10/407,010, filed on Apr. 3, 2003, now Pat. No. 7,563,281.

(51) Int. Cl.
*A61F 2/44* (2006.01)
(52) U.S. Cl. ............... 623/17.14; 623/17.15; 623/17.16
(58) Field of Classification Search ............. 623/17.14, 623/17.15, 17.16
See application file for complete search history.

(56) References Cited

U.S. PATENT DOCUMENTS

| | | | |
|---|---|---|---|
| 4,554,914 A | 11/1985 | Kapp et al. | |
| 4,599,086 A | 7/1986 | Doty | |
| 4,636,217 A | 1/1987 | Ogilvie et al. | |
| 4,759,769 A | 7/1988 | Hedman et al. | |
| 4,904,261 A | 2/1990 | Dove et al. | |
| 5,062,850 A * | 11/1991 | MacMillan et al. | 623/17.11 |
| 5,108,395 A | 4/1992 | Laurain | |
| 5,192,327 A | 3/1993 | Brantigan | |
| 5,336,223 A | 8/1994 | Rogers | |
| 5,413,602 A | 5/1995 | Metz-Stavenhagen | |
| 5,571,190 A | 11/1996 | Ulrich et al. | |
| 5,620,458 A | 4/1997 | Green et al. | |
| 5,645,084 A | 7/1997 | McKay | |
| 6,086,613 A | 7/2000 | Camino et al. | |
| 6,106,557 A | 8/2000 | Robioneck et al. | |
| 6,159,211 A | 12/2000 | Boriani et al. | |
| 6,193,720 B1 | 2/2001 | Yuan et al. | |
| 6,235,034 B1 | 5/2001 | Bray | |
| 6,296,665 B1 | 10/2001 | Strnad et al. | |
| 6,299,644 B1 | 10/2001 | Vanderschot | |
| 6,375,681 B1 | 4/2002 | Truscott | |
| 6,375,683 B1 | 4/2002 | Crozet et al. | |
| 6,626,943 B2 * | 9/2003 | Eberlein et al. | 623/17.15 |
| 6,989,032 B2 * | 1/2006 | Errico et al. | 623/17.14 |
| 7,320,708 B1 * | 1/2008 | Bernstein | 623/17.15 |
| 2002/0045904 A1 | 4/2002 | Fuss et al. | |

FOREIGN PATENT DOCUMENTS

| | | |
|---|---|---|
| DE | 94 13 778 U1 | 2/1996 |
| EP | 1 080 703 A3 | 1/2002 |
| FR | 2636227 A1 | 3/1990 |

* cited by examiner

*Primary Examiner* — Corrine M McDermott
*Assistant Examiner* — Christopher D Prone

(57) ABSTRACT

An apparatus and method for supporting upper and lower vertebral bodies, including first and second end members adapted for engagement with the vertebral bodies, and at least one elongate support member coupled between the end members to maintain an axial space between the vertebral bodies. In one aspect of the invention, each of the end members has a parametrical or horseshoe-shaped configuration extending about an open inner region and defining a lateral passage communicating with the open inner region to facilitate insertion of the apparatus or the individual end members into the intervertebral space via a posterior surgical approach. In a further aspect of the invention, a fusion member is positioned within the axial space to promote bony fusion between the upper and lower vertebral bodies.

30 Claims, 10 Drawing Sheets

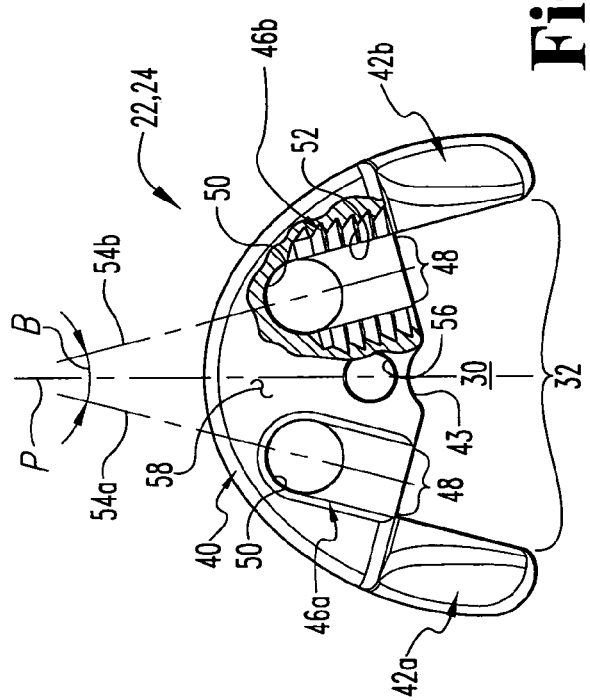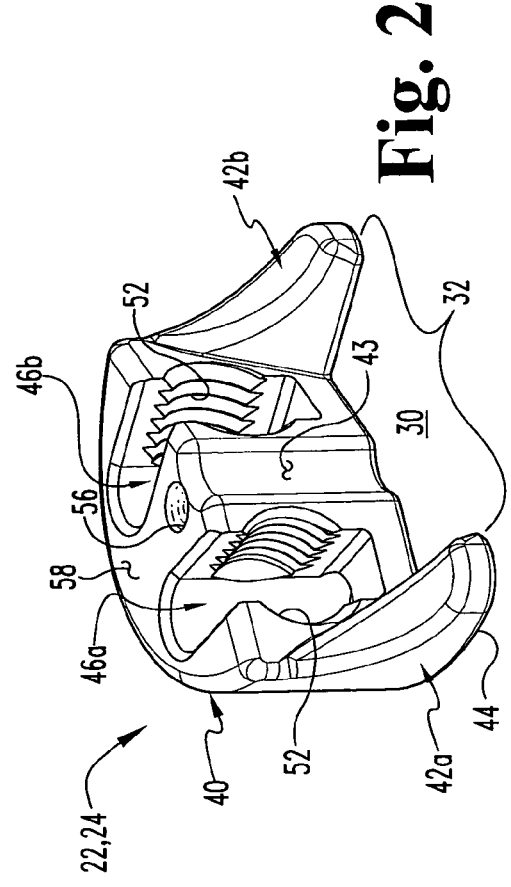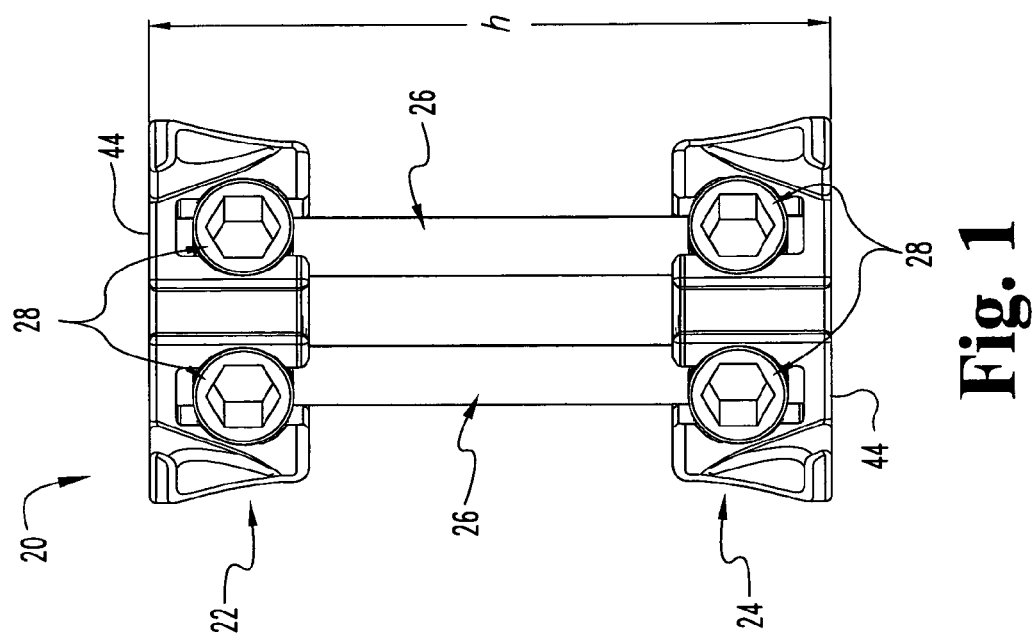

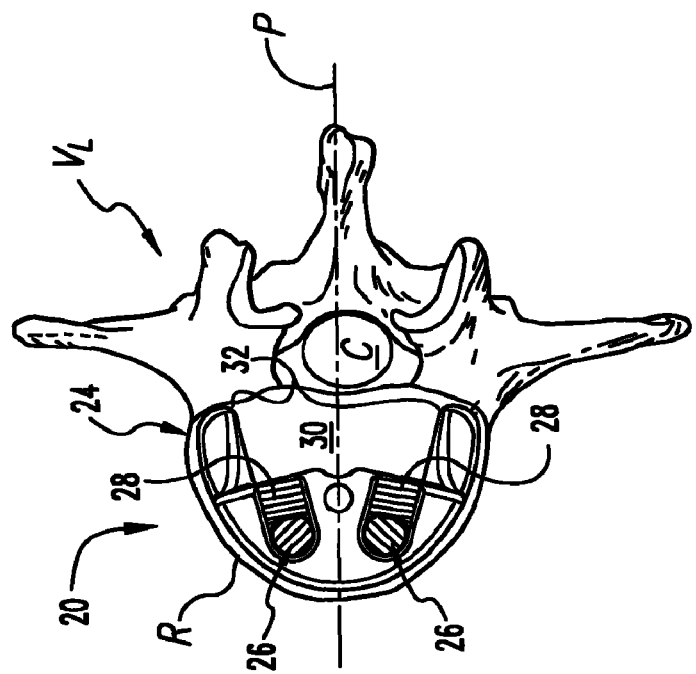
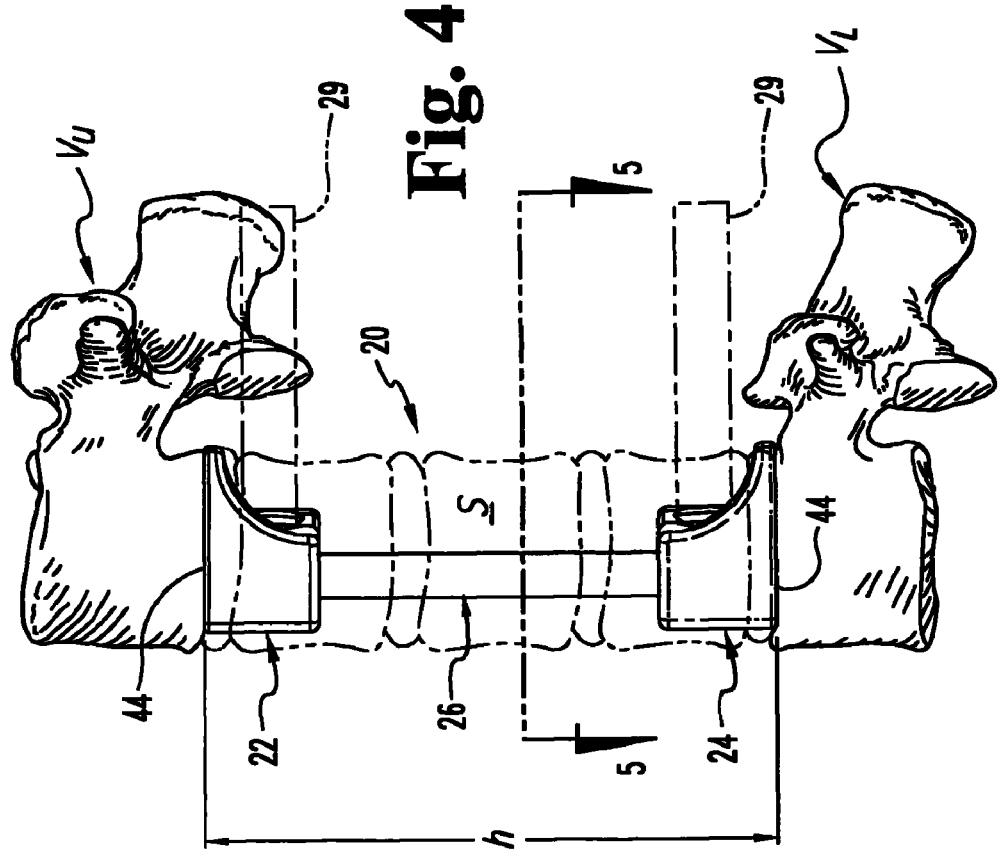

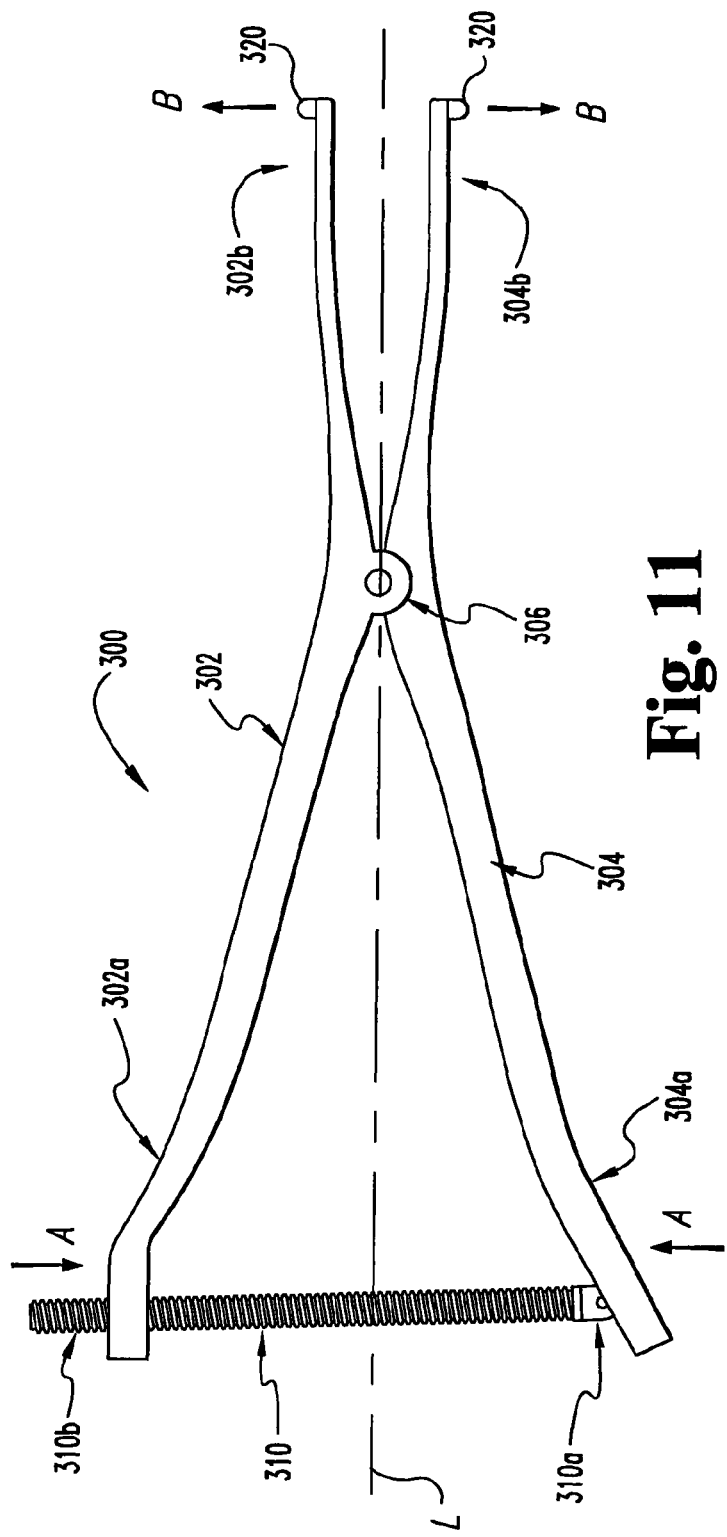
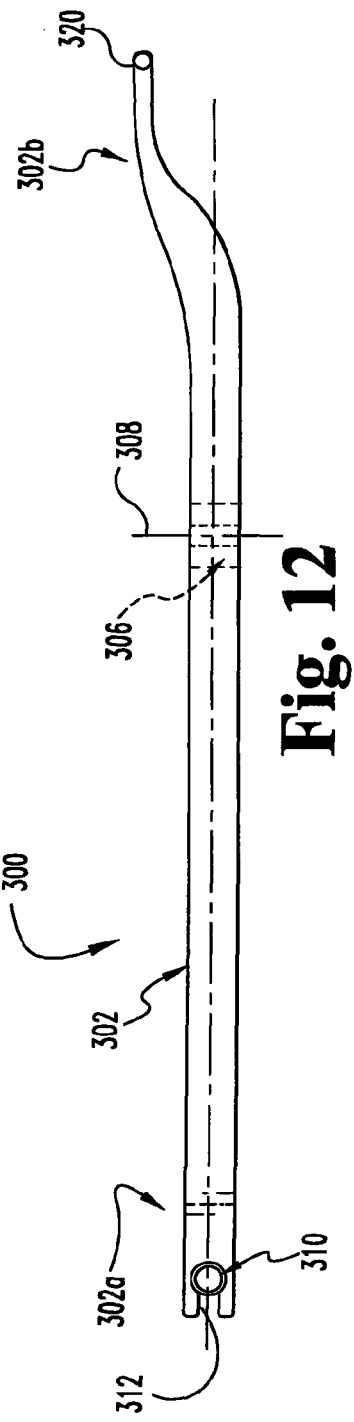
Fig. 11
Fig. 12

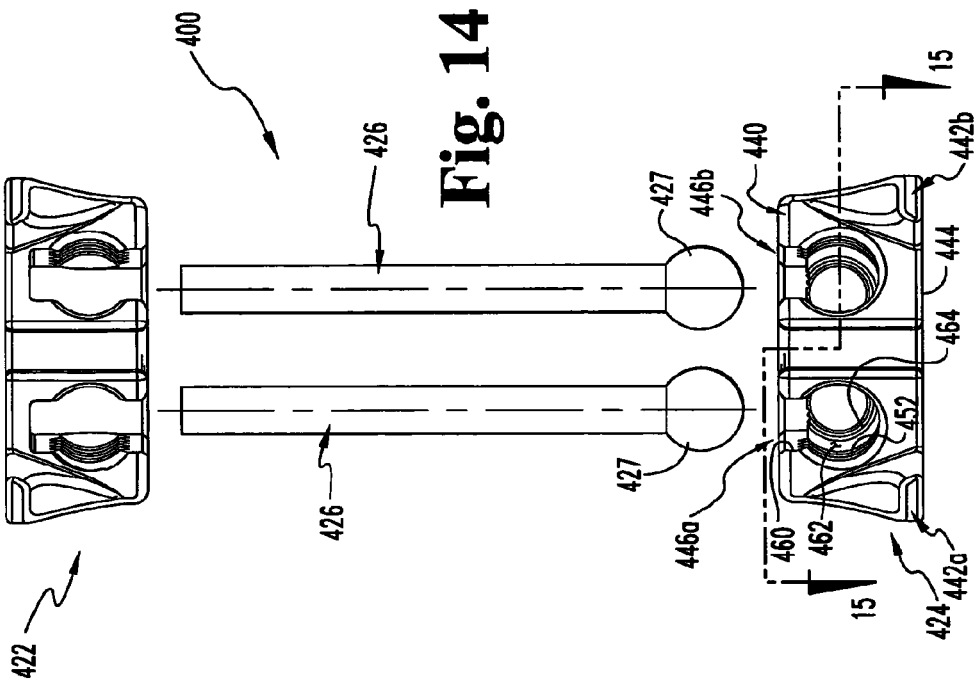
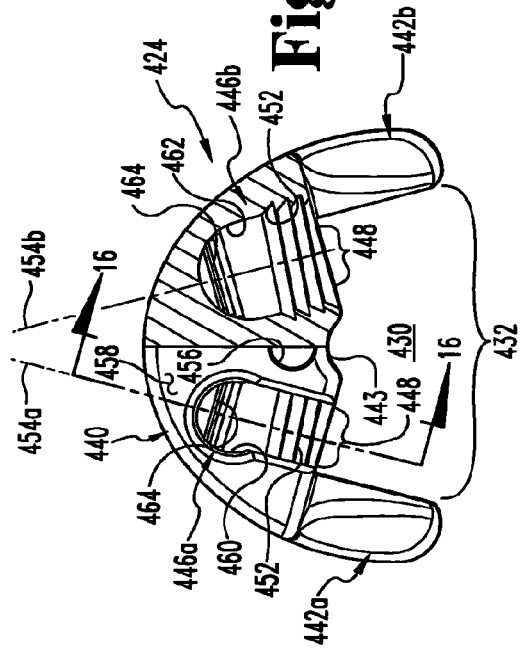
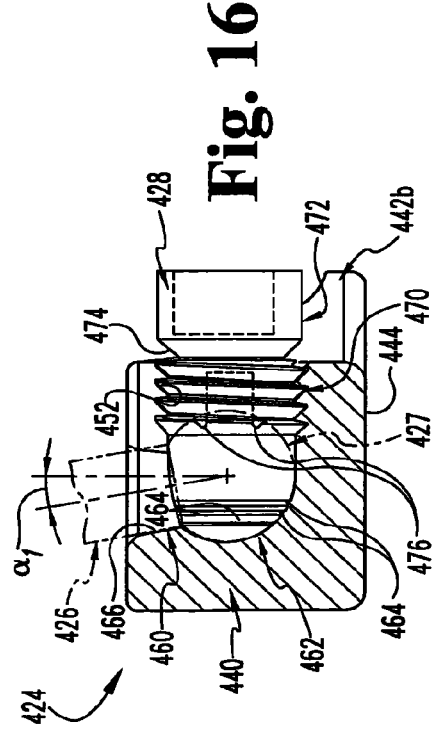

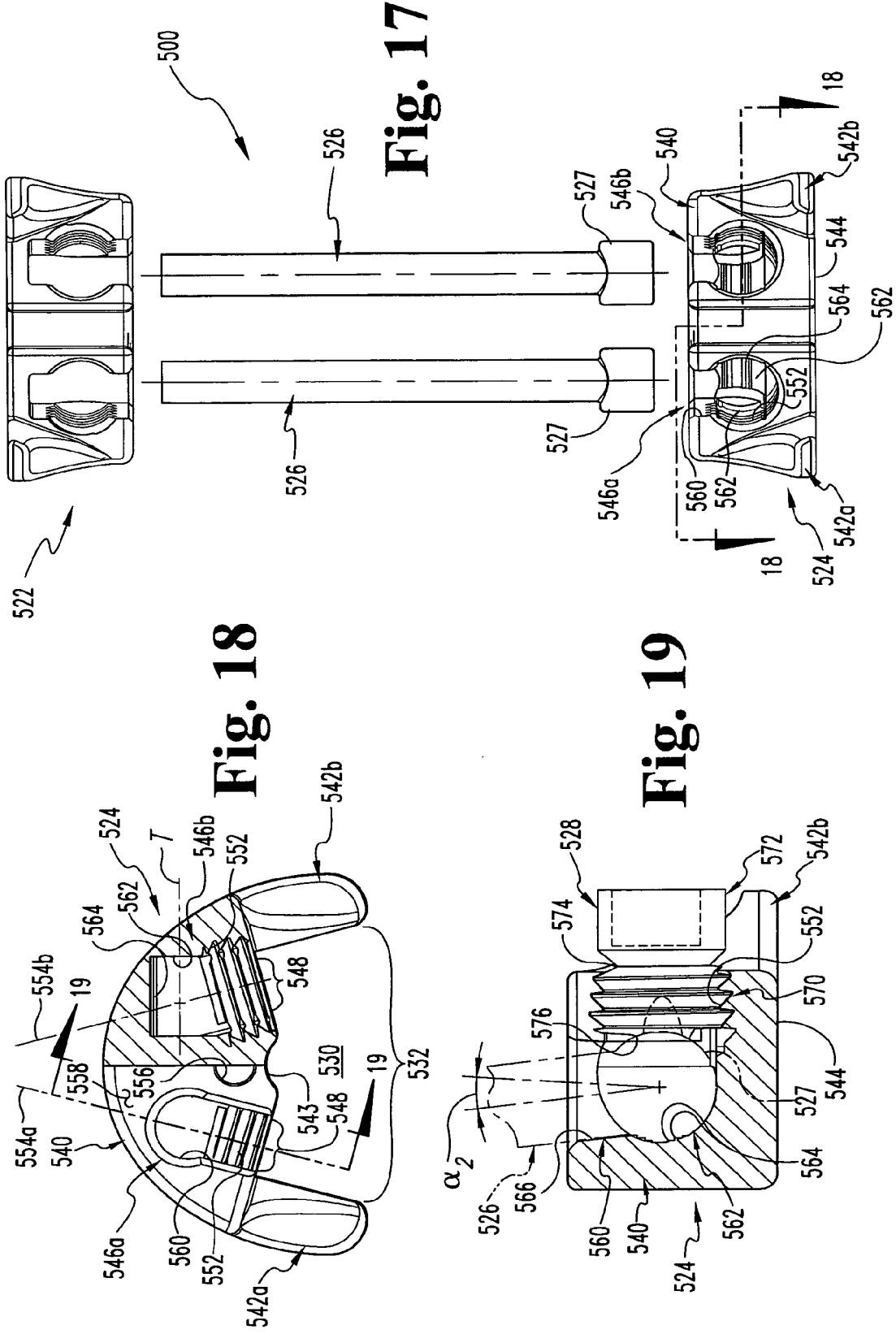

APPARATUS AND METHOD FOR SUPPORTING VERTEBRAL BODIES

The present application is a continuation of U.S. patent application Ser. No. 10/407,010 filed on Apr. 3, 2003 and now issued as U.S. Pat. No. 7,563,281, the contents of which are hereby incorporated by reference in their entirety.

FIELD OF THE INVENTION

The present invention generally relates to spinal implants, and more particularly relates to an apparatus and method for supporting an axial space between vertebral bodies following a vertebrectomy.

BACKGROUND

Various portions of the spinal column may become displaced or damaged due to trauma, disease or aging. Treatment procedures may involve removal of at least a portion of one or more vertebral bodies and/or intervertebral disc tissue. Several techniques are currently available for restoring and maintaining the axial space between two vertebral bodies following removal of vertebral bone and/or tissue from the area between the vertebral bodies. Restoration and support of the axial space is sometimes accomplished by attaching one or more plates and/or rods to outer surfaces of the vertebral bodies to bridge the intervertebral space. In other instances, an implant is inserted into the intervertebral space to provide the requisite amount of axial support. Additionally, a bone growth inducing material is sometimes introduced into the intervertebral space to facilitate the formation of a solid bony connection between the vertebral bodies. For example, previous vertebral body replacement implants include allograft, silicone tubing filled with cement, cages and other types of fusion devices or materials. However, adjustability is a feature that most of these techniques fail to provide. Subsidence into the adjacent vertebral bodies is also a drawback prevalent in previous vertebrectomy options.

Access to a displaced or damaged portion of the spinal column may be accomplished via several approaches. One approach is to gain access to the anterior portion of the spine through the patient's chest or abdomen. However, significant morbidity may ensue and many vertebral levels are not readily accessible via an anterior approach, particularly with regard to the upper thoracic or upper lumbar vertebral levels. A posterior approach may also be used and provides a number of advantages, but may be associated with considerable difficulty in the reconstruction of the spinal column. In particular, the presence of the spinal cord and the inherent risks associated with retraction and manipulation of this structure limits access to the intervertebral space that lies anterior to the spinal cord. While it is desirable that implants should distribute the loads of the spinal column evenly and widely across the vertebral endplates, the introduction of currently available implants requires considerable retraction and/or manipulation of the spinal cord, thereby increasing the potential for complications.

Thus, there is a general need in the industry to provide an improved apparatus and method for supporting vertebral bodies following a vertebrectomy. The present invention meets this need and provides other benefits and advantages in a novel and unobvious manner.

BRIEF DESCRIPTION OF THE FIGURES

FIG. 1 is an end elevational view of a cage assembly according to one embodiment of the present invention.

FIG. 2 is a side perspective view of an end member according to one embodiment of the present invention for use in association with the cage assembly illustrated in FIG. 1.

FIG. 3 is a top plan view, partially in section, of the end member illustrated in FIG. 2.

FIG. 4 is a side elevational view of the cage assembly illustrated in FIG. 1, as positioned between upper and lower vertebral bodies.

FIG. 5 is a cross sectional view of the cage assembly illustrated in FIG. 4, as viewed along line 5-5 of FIG. 4.

FIG. 11 is a side view of a distractor instrument according to one embodiment of the present invention for use in association with the cage assembly illustrated in FIG. 1.

FIG. 12 is a top plan view of the distractor instrument illustrated in FIG. 11.

FIG. 13b is a cross-sectional view of the distal end portions of the distractor instrument as engaged with the cage assembly illustrated in FIG. 13a, as viewed along line 13b-13b of FIG. 13a.

FIG. 14 is an exploded posterior elevational view of a cage assembly according to another embodiment of the present invention having a multi-axial configuration.

FIG. 15 is a top plan view, partially in section, of a multi-axial end member according to one embodiment of the invention for use in association with the cage assembly illustrated in FIG. 14, as viewed along line 15-15 of FIG. 14.

FIG. 16 is a cross sectional view of the multi-axial end member illustrated in FIG. 15, as viewed along line 16-16 of FIG. 15.

FIG. 17 is an exploded posterior elevational view of a cage assembly according to another embodiment of the present invention having a mono-axial configuration.

FIG. 18 is a top plan view, partially in section, of a mono-axial end member according to one embodiment of the invention for use in association with the cage assembly illustrated in FIG. 17, as viewed along line 18-18 of FIG. 17.

FIG. 19 is a cross sectional view of the mono-axial end member illustrated in FIG. 18, as viewed along line 19-19 of FIG. 18.

SUMMARY OF THE INVENTION

Figure 6A:
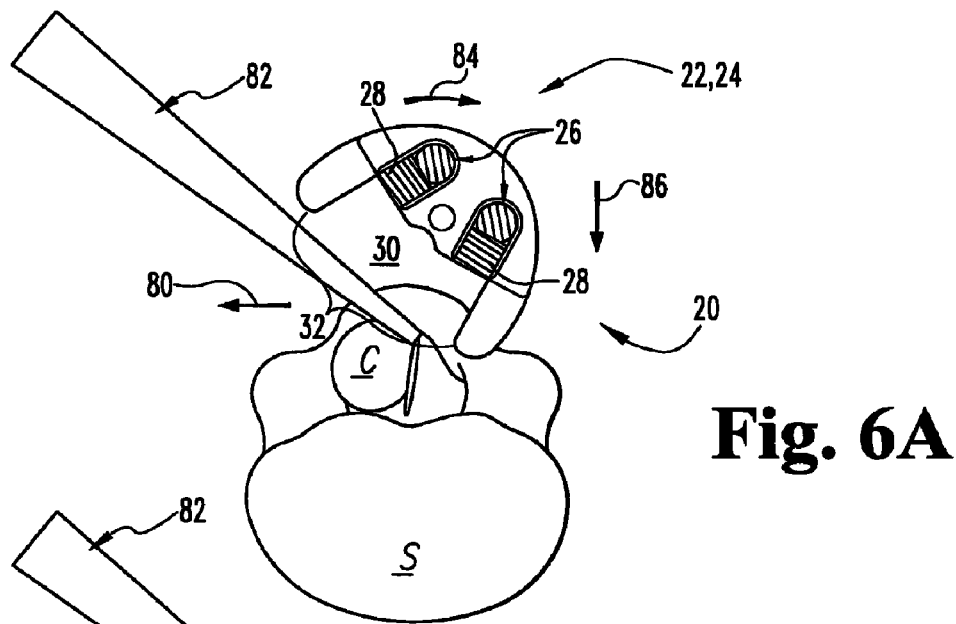
FIGS. 6A-6C are illustrations of a method according to one embodiment of the present invention for inserting the cage assembly illustrated in FIG. 1 between the upper and lower vertebral bodies using a posterior surgical approach.

According to one form of the present invention, an apparatus is provided for supporting vertebral bodies, including a first end member adapted to engage a lower endplate of a first vertebral body, a second end member adapted to engage an upper endplate of a second vertebral body, and at least one elongate support member coupled between the first and second end members to maintain an axial space between the first and second vertebral bodies. Each of the first and second end members has a parametrical configuration extending about an open inner region and defining a lateral passage communicating with the open inner region.

According to another form of the present invention, an apparatus is provided for supporting vertebral bodies, including a first horseshoe-shaped member adapted to engage a first vertebral body, a second horseshoe-shaped member adapted to engage a second vertebral body, and at least one elongate support member coupled between the first and second horseshoe-shaped members to maintain an axial space between the first and second vertebral bodies.

According to another form of the present invention, an apparatus is provided for supporting vertebral bodies, including a first end member adapted to engage a first vertebral body, a second end member adapted to engage a second vertebral body, at least one elongate support member coupled between the first and second end members to maintain an axial space between the first and second vertebral bodies, and a fusion member positioned within the axial space to promote bony fusion between the first and second vertebral bodies.

According to another form of the present invention, a method for supporting vertebral bodies of a spinal column is provided, including providing first and second end members each having a parametrical configuration extending about an open inner region and defining a lateral passage communicating with the open inner region, and providing at least one elongate support member. The method further includes positioning the first end member adjacent a first vertebral body, positioning the second end member adjacent a second vertebral body, and coupling the elongate support member between the first and second end members to maintain an axial space between the first and second vertebral bodies.

According to another form of the present invention, a method for supporting vertebral bodies of a spinal column is provided, including providing first and second end members each including an axial passage extending therethrough, providing at least one elongate support member, and providing fusion material. The method further includes positioning the first end member in the axial space and adjacent an endplate of the first vertebral body with the axial passage of the first end member arranged along the sagittal plane of the spinal column, positioning the second end member in the axial space and adjacent an endplate of the second vertebral body with the axial passage of the second end member arranged along the sagittal plane of the spinal column, coupling the elongate support member between the first and second end members to maintain the axial space between the first and second vertebral bodies, and positioning the fusion material within the axial space adjacent the axial passages of the first and second end members to promote bony fusion between the endplates of the first and second vertebral bodies.

It is one object of the present invention to provide an improved apparatus and method for supporting vertebral bodies.

Further objects, features, advantages, benefits, and further aspects of the present invention will become apparent from the drawings and description contained herein.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation on the scope of the invention is hereby intended, such alterations and further modifications in the illustrated devices and methods, and such further applications of the principles of the invention as illustrated herein being contemplated as would normally occur to one skilled in the art to which the invention relates.

Referring to FIG. 1, shown therein is an apparatus 20 for supporting vertebral bodies according to one form of the present invention. In one embodiment, the apparatus 20 is a modular vertebrectomy cage assembly positionable within an intervertebral space to span one or more vertebral levels along the longitudinal axis of the spinal column. Although the illustrated embodiment of the cage assembly 20 spans three vertebral levels (FIG. 4), it should be understood that the cage assembly 20 may be configured to span a single vertebral level, two vertebral levels, or four or more vertebral levels.

The cage assembly 20 is generally comprised of a first end member 22, a second end member 24, and one or more elongate support members or rods 26 coupled between the first and second end members 22, 24. Although the cage assembly 20 has been illustrated as including a pair of support rods 26, it should be understood that any number of support rods may be used, including a single support rod or three or more support rods. In one embodiment of the invention, the support rods 26 have a solid configuration and a generally cylindrical shape. However, it should be understood that other shapes and configurations of the support rods 26 are also contemplated. For example, in other embodiments of the invention, the support rods 26 may be configured as hollow tubes. In further embodiments, the support rods 26 may take on other cross-sectional shapes, such as, for example, rectangular, hexagonal or elliptical cross-sectional shapes, or any other cross-sectional shape that would occur to one of skill in the art.

The end members 22, 24 are adapted to engage the endplates of upper and lower vertebral bodies $V_U$, $V_L$ (FIG. 4). The support rods 26 are engaged between the end members 22, 24 to maintain an intervertebral axial space S between the upper and lower vertebral bodies $V_U$, $V_L$ following the removal of one or more vertebral levels (shown in phantom). In one embodiment of the invention, the support rods 26 are engaged to the end members 22, 24 via a number of fasteners, such as, for example, set screws 28. However, as will be discussed in greater detail below, it should be understood that other means for engaging the support rods 26 to the end members 22, 24 are also contemplated as falling within the scope of the present invention.

In one embodiment of the invention, the end members 22, 24 are formed of a radiolucent material, such as, for example, a carbon fiber material. In this manner, x-ray viewing of the intervertebral space S and the vertebral endplates subsequent to implantation of the cage assembly 20 will be relatively unobstructed. In further embodiments of the invention, the end members 22, 24 may be formed of other suitable materials, such as, for example, stainless steel, titanium or other biocompatible materials. In another embodiment of the invention, the support rods 26 are formed of stainless steel, titanium or other biocompatible materials. In further embodiments, the support rods 26 and/or any other component of the cage assembly 20 may be formed of a radiolucent material, such as, for example, a carbon fiber material.

Referring now to FIGS. 2 and 3, shown therein are further details regarding the end members 22, 24. With specific regard to the cage assembly 20, the end members 22, 24 are configured identical to one another. However, it should be understood that in other embodiments of the invention, the end members 22, 24 can take on different configurations, examples of which will be illustrated and described below.

In a preferred embodiment of the invention, each of the end members 22, 24 has a parametrical configuration extending about an open inner region 30 and defining a lateral passage 32 communicating with open inner region 30. In one embodiment, the end members 22, 24 are generally horseshoe-shaped. In other embodiments, the end members 22, 24 could also be described as being U-shaped, C-shaped, V-shaped, semi-circular shaped, semi-oval shaped, or other terms that could be used to describe a shaped element defining an open inner region and a lateral passage communicating therewith. In further embodiments of the invention, the end members 22, 24 may take on other types of hollow configurations, such as, for example, a circular shape, semi-oval shape, kidney shape, D-shape, or any other shape that would occur to one of skill in the art. In still other embodiments of the invention, the end members 22, 24 may take on substantially solid configurations, such as, for example, block-like or plate-like configurations that do not define an open inner region.

It should further be appreciated that the size and/or configuration of the end members 22, 24 may be specifically designed to accommodate any particular region of the spinal column and/or any particular vertebral level. For example, in embodiments of the invention associated with the upper thoracic or cervical region of the spine, the end members 22, 24 may be designed to have a D-shaped configuration, whereas embodiments of the invention associated with the lumbar region of the spine may be configured to have a horseshoe-shape, a U-shape, or other types of open-sided configurations.

In one embodiment of the invention, the end members 22, 24 have a lateral profile that is substantially complementary to the size and shape of the peripheral portion or outlying region of the vertebral bodies, such as the cortical rim or the apophyseal ring of the vertebral endplates. For example, as illustrated in FIG. 5, the outer perimeter of the end member 24 is preferably disposed generally above the inner edge of the cortical rim R of the lower vertebral body $V_L$. In this manner, at least a portion of the end members 22, 24 is engaged against the cortical region of the vertebral endplates, thereby minimizing the likelihood of subsidence into the relatively softer cancellous region of the upper and lower vertebral bodies $V_U$, $V_L$ following implantation of the cage assembly 20 within the intervertebral space S. Additionally, the parametrical configuration of the end members 22, 24 in combination with the relatively large surface area of the end members 22, 24 engaged against the vertebral endplates enhances the overall stability of the cage assembly 20. Moreover, the open inner region 30 defined by each of the end member 22, 24 provides significant exposure of the vertebral endplates to enhance bony fusion between the upper and lower vertebral bodies $V_U$, $V_L$, the details of which will be discussed below.

In one embodiment of the invention, the end members 22, 24 include a main body or base portion 40 and a pair of oppositely disposed wings or side portions 42a, 42b extending from the base portion 40. The base portion 40 and the side portions 42a, 42b cooperate to define the open inner region 30, with the distal ends of the side portions 42a, 42b defining the lateral passage 32 therebetween. The lateral surface of the base portion 40 facing the open inner region 30 defines a recessed area 43 to eliminate the presence of sharp corners and which also serves to provide for a slightly larger open inner region 30 which correspondingly increases exposure of the vertebral endplates to enhance fusion capabilities.

In one embodiment, the upper/lower engaging surface 44 of the end members 22, 24 is substantially planar and defines surface features and/or a number of anchor elements adapted for engagement with the vertebral endplates to inhibit movement of the end members 22, 24 relative to the upper and lower vertebral bodies $V_U$, $V_L$. For example, in one embodiment, the upper/lower engaging surfaces 44 may be roughened, such as, for example, by knurling and/or etching (e.g., photochemical etching). In other embodiments, various types of projections or protrusions may extend from the upper/lower engaging surfaces 44, such as, for example, a number of spikes, ridges, teeth, axial grooves, checkerboard-type grooves, or any other type of anchoring element that would occur to one of skill in the art. Although the upper/lower engaging surfaces 44 of the end members 22, 24 are illustrated as being arranged substantially parallel to one another when the cage assembly 20 is fully assembled (FIG. 1), it should be understood that the upper/lower engaging surfaces 44 may be tapered relative to one another to more closely conform with the anatomical curvature of the spine at the surgical site (e.g., the angle of lordosis or kyphosis). It should also be understood that the support rods 26 may be bent and/or provided with a predetermined curvature to more closely match the configuration of the cage assembly 20 with the anatomical curvature of the spine at the surgical site.

The base portion 40 of the end members 22, 24 defines a pair of sockets or receptacles 46a, 46b sized to receive end portions of respective support rods 26 therein. It should be understood, however, that the base portion 40 may define any number of sockets or receptacles for receiving a corresponding number of support rods, including a single socket or three or more sockets. In one embodiment of the invention, the sockets 46a, 46b each define a lateral opening 48 sized to receive the end portion of a corresponding support rod 26 therethrough. In this manner, the end portions of the support rods 26 may be laterally inserted into the sockets 46a, 46b via a side-loading technique, preferably from a posterior direction. Lateral insertion of the support rods 26 may be particularly advantageous when assembling the cage assembly 20 in situ within the intervertebral space S. The lateral openings 48 are preferably general aligned with the lateral passage 32 defined between the side portions 42a, 42b to further enhance the ability to laterally insert the support rods 26 into the sockets 46a, 46b. In a further embodiment of the invention, the sockets 46a, 46b each define a thru-opening 50 extending axially through the end members 22, 24 and sized to slidably receive the end portion of a corresponding support rod 26 therethrough. This embodiment of the invention may also be particularly advantageous when assembling the cage assembly 20 in situ within the intervertebral space S.

Figure 7:
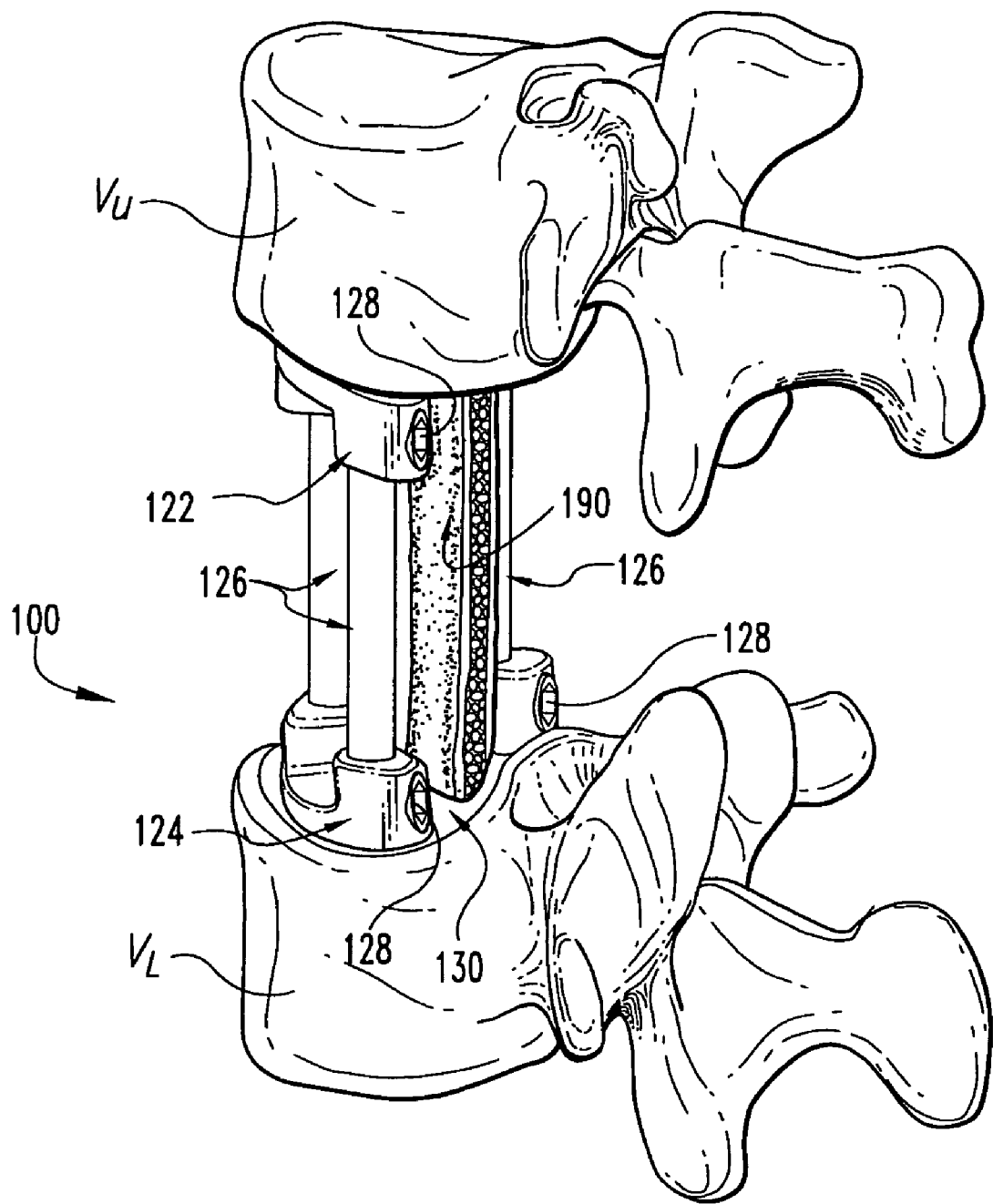
FIG. 7 is a perspective elevational view of a cage assembly according to another embodiment of the present invention, as positioned between upper and lower vertebral bodies and with a fibular strut augmented within an interior region of the cage assembly for promoting bone growth between the upper and lower vertebral bodies.
Figure 8:
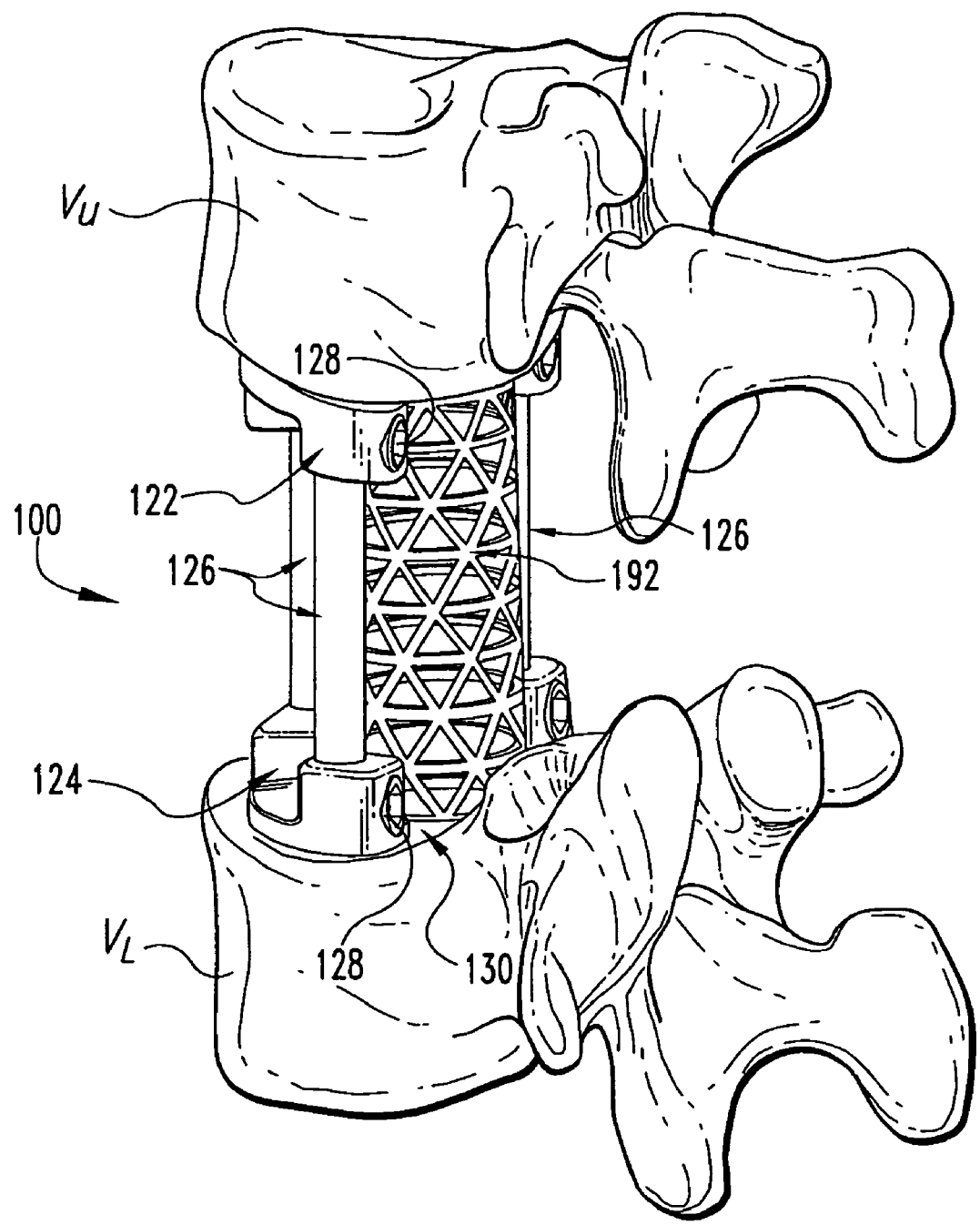
FIG. 8 is a perspective elevational view of a cage assembly according to another embodiment of the present invention, as positioned between upper and lower vertebral bodies and with a hollow mesh cage member positioned within an interior region of the cage assembly for promoting bone growth between the upper and lower vertebral bodies.
Figure 9:
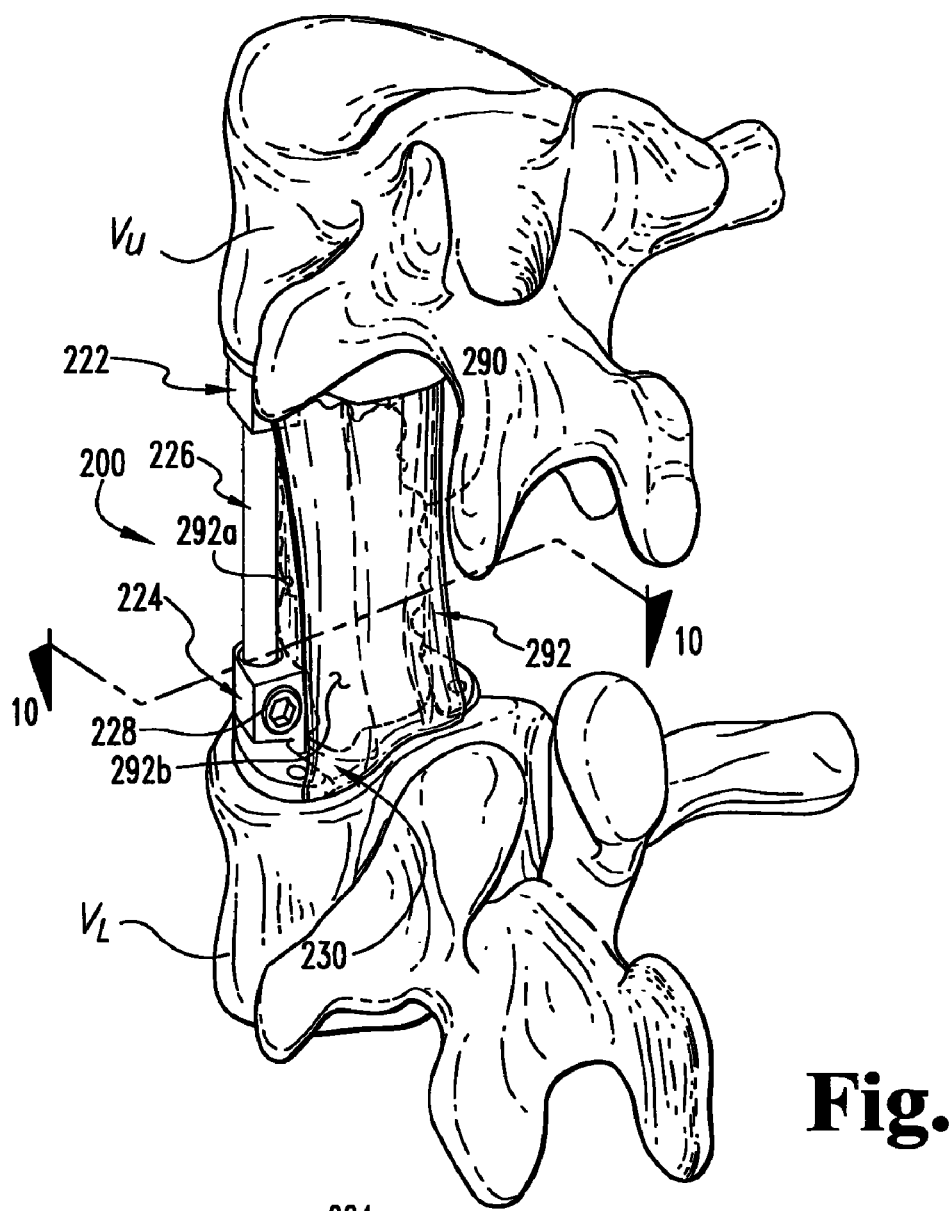
FIG. 9 is a perspective elevational view of a cage assembly according to another embodiment of the present invention, as positioned between upper and lower vertebral bodies and with graft material contained by a resorbable film positioned within an interior region of the cage assembly for promoting bone growth between the upper and lower vertebral bodies.
Figure 10:
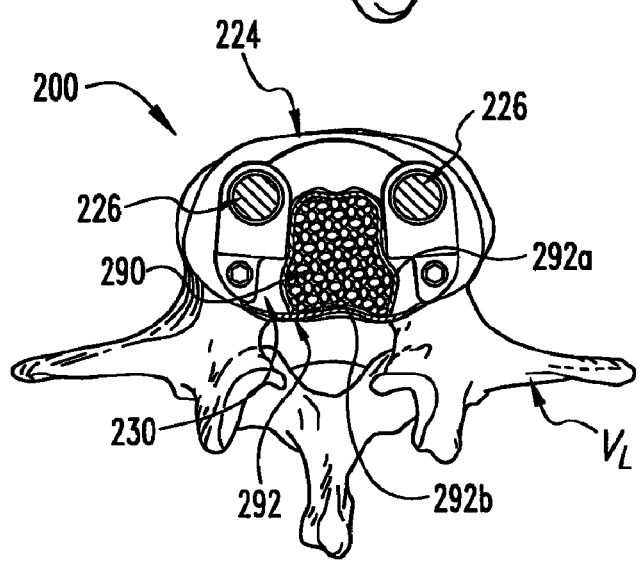
FIG. 10 is a cross-sectional view of the cage assembly illustrated in FIG. 9.

Although a specific embodiment of the sockets 46a, 46b has been illustrated and described herein, it should be understood that sockets 46a, 46b may take on other alternative configurations. For example, as illustrated in FIGS. 7 and 8, the end members 122, 124 associated with the cage assembly 100 define sockets that do not define lateral openings, but instead define a closed configuration. As should be appreciated, in this embodiment, engagement of the support rods 126 with the end members 122, 124 would occur via axial insertion of the end portions of the support rods 126 into the sockets of the end members 122, 124. Similarly, as illustrated in FIGS. 9 and 10, the end members 222, 224 associated with the cage assembly 200 also define a closed configuration. Additionally, although the sockets 46a, 46b have been illustrated as defining an axial thru-opening 50, in other embodiments of the invention, the sockets 46a, 46b may alternative define a closed or blind bottom configuration.

In the illustrated embodiment of the invention, the sockets 46a, 46b each define a laterally-extending threaded aperture 52 that is adapted to threadingly receive a corresponding set screw 28 therein (FIG. 1). Once the end portions of the support members 26 are inserted into the sockets 46a, 46b, the set screws 28 are threaded into the apertures 52 and into engagement with the end portions of the support rods 26 to securely couple the end members 22, 24 thereto. The threaded apertures 52 are preferably generally aligned with the lateral passage 32 defined between the side portions 42a, 42b to provide substantially uninhibited access to the set screws 28 to facilitate tightening of the set screws 28 into the end members 22, 24. Once again, this setup may be particularly advantageous when assembling the cage assembly 20 in situ within the intervertebral space S.

In one embodiment, the threaded aperture 52 extend along axes 54a, 54b that are outwardly tapered relative to one another and to the sagittal plane P extending along the spinal column when the cage assembly 20 is positioned within the intervertebral space S (FIG. 5). Arrangement of the set screw axes 54a, 54b in a diverging relationship tends to enhance the accessibility of the set screws 28. In one embodiment of the invention, the set screw axes 54a, 54b are arranged to define an included angle $\beta$ of about ten (10) to twenty (20) degrees. In a specific embodiment, the included angle $\beta$ is about sixteen (16) degrees. However, it should be understood that other arrangements of the axes 54a, 54b are also contemplated as falling within the scope of the present invention, including parallel arrangements.

In one embodiment of the invention, the set screws 28 are of the break-off type, including a head portion that is selectively removable from a threaded shank portion, the details of which will be discussed below. However, it should be understood that other types and configurations of set screws are also contemplated. It should also be understood that although set screws have been illustrated and described as the preferred means for coupling the support rods 26 to the end members 22, 24, other elements or devices may alternatively be used, such as, for example, various types of fasteners, snap rings, collets, collars, wedges, or any other type of element or device capable of coupling the support rods 26 to the end members 22, 24. Alternatively, either or both end portions of each support rod 26 may be threadingly engaged with a corresponding threaded portion defined by each of the end members 22, 24.

In a further aspect of the invention, the end members 22, 24 each define a tool receiving aperture 56. The tool receiving apertures 56 are sized and shaped to receive a corresponding end portion of a tool or instrument therein to facilitate insertion of the cage assembly 20 into the intervertebral space S, manipulation of the end members 22, 24 relative to the support rods 26, and/or distraction of the intervertebral space S. Although the tool receiving apertures 56 are illustrated as having a generally circular configuration, other shapes and configurations are also contemplated, such as, for example, hexagonal or rectangular configurations. In the illustrated embodiment of the invention, the tool receiving apertures 56 are formed in the base portion 40 of the end members 22, 24 through an inwardly facing surface 58 (the surface opposite the outer engaging surface 44). However, it should be understood that the tool receiving apertures 56 may be formed in other portions of the end members 22, 24, including the side portions 42a, 42b (see FIGS. 9 and 10), and through other surfaces, such as the laterally extending surfaces of the end members 22, 24.

In the illustrated embodiment of the invention, the sockets 46a, 46b associated with the end members 22, 24 have been depicted as having an axially extending cylindrical configuration adapted to receive a correspondingly shaped end portion of a support rod 26 therein. In this manner, when the support rods 26 are properly positioned within the sockets 46a, 46b, the support rods 26 will be arranged at a predetermined angular orientation relative to the end members 22, 24, which in turn arranges the end members 22, 24 at predetermined angular orientations relative to one another. However, it should be understood that the sockets 46a, 46b and/or the end portions of the support rods 26 may be configured such that the angular orientation of the support rods 26 relative to the end members 22, 24 may be varied or adjusted to correspondingly arrange the end members 22, 24 at select angular orientations relative to one another.

For example, referring to FIGS. 14-16, shown therein is a cage assembly 400 according to another form of the present invention. The cage assembly 400 is generally comprised of a first end member 422, a second end member 424, and one or more elongate support members or rods 426 coupled between the first and second end members 422, 424. As will be discussed below, the cage assembly 400 is configured to allow the support rods 426 to pivot relative to at least one of the end members 422, 424, and includes a number of fasteners, such as, for example, set screws 428 (FIG. 16) adapted to lock the support rods 426 at a select angular orientation relative to the end members 422, 424. Although the cage assembly 400 has been illustrated as including a pair of support rods 426, it should be understood that any number of support rods may be used, including a single support rod or three or more support rods.

The support rocs 426 are configured similar to the support rods 26 illustrated and described above with regard to the cage assembly 20, having a solid configuration and a substantially cylindrical shape. However, unlike the support rods 26, one end portion of the support rods 426 defines a spherical-shaped end portion 427, the purpose of which will be discussed below, with the opposite end portion defining an axially extending cylindrical configuration. In this manner, the end portion defining the axially extending cylindrical configuration may be cut to an appropriate length that provides the cage assembly 400 with an overall height which closely matches the natural or corrected height of the intervertebral space S. It should be understood, however, that in other embodiments of the invention, each end portion of the support rods 426 may define a spherical-shaped end portion 427.

The end member 422 is configured substantially identical to the end members 22, 24 illustrated and described above with regard to the cage assembly 20, including sockets configured similar to sockets 46a, 46b for receiving the axially extending cylindrical end portions of the support rods 426 therein. In many regards, the end member 424 is configured similar to the end member 422. For example, the end member 424 has a parametrical configuration extending about an open inner region 430 and defining a lateral passage 432 communicating with the open inner region 430. Additionally, the end member 424 has a base portion 440, a pair of oppositely disposed wings or side portions 442a, 442b, an upper/lower engaging surface 444, a pair of sockets or receptacles 446a, 446b defining lateral openings 448, threaded aperture 452 extending along axes 454a, 454b, and a tool receiving aperture 456. However, unlike end member 422, the end member 424 is configured to pivotally receive the spherical-shaped end portions 427 of the support rods 426 to allow for relative pivotal movement between the support rods 426 and the end member 424, the details of which will follow.

In one embodiment of the invention, the sockets 446a, 446b each include an axially extending cylindrical-shaped portion 460 and a spherical-shaped recessed portion 462 sized and shaped to receive the spherical-shaped end portion 427 of a respective support rod 426 therein. In this manner, the support rods 426 are allowed to pivot relative to the end member 424 about multiple axes, and in any direction relative to the end member 424, within a range of angular orientations. This multi-axial configuration allows the support rods 426 to be arranged at various angular orientations relative to the end member 424, which in turn allows the end member 424 to be arranged at various angular orientations relative to the end member 422.

As should be appreciated, arranging the end members 424 at a select angular orientation relative to the end member 422 may be particularly useful to more closely match the configuration of the cage assembly 400 with the anatomical features associated with the intervertebral space S (e.g., the angle of lordosis or kyphosis). As should also be appreciated, each of the support rods 426 need not necessarily have the same overall length. Instead, the support rods 426 may define different lengths to allow for more precise adjustment of the angular orientation between the end members 422, 424, particularly in cases where the support rods 426 are not arranged along a common plane, such as, for example, the support rods 126 associated with the cage assembly 100 (FIGS. 7 and 8). Additionally, the support rods 426 may be curved or bent to provide further adjustment to the angular orientation between the end members 422, 424.

As illustrated in FIG. 16, the support rod 426 is allowed to pivot up to an angle $\alpha_1$ in any direction, limited only by engagement of the support rod 426 against a surface 466 defined by the cylindrical portion 460 of the sockets 446a, 446b. In one embodiment of the invention, the surface 466 is tapered at an angle approximately equal to the angle $\alpha_1$. In a further embodiment of the invention, at least a portion of the spherical-shaped recessed portion 462 of the sockets 446a, 446b defines a number of surface projections or protrusions 464, such as, for example, a series of ridges or teeth and/or spikes, the purpose of which will be discussed below. In one embodiment, the surface projections or protrusions 464 are positioned generally opposite the threaded aperture 452; however, it should be understood that other positions configurations are also contemplated.

In the illustrated embodiment of the invention, the threaded aperture 452 communicating with the sockets 446a, 446b has a diameter approximately equal to or slightly greater than the diameter of the spherical-shaped recessed portion 462. In this manner, the spherical-shaped end portions 427 of the support rod 426 may be laterally inserted into the sockets 446a, 446b via a side-loading technique, which may be particularly advantageous when assembling the cage assembly 400 in situ within the intervertebral space S. In a further embodiment of the invention, the cylindrical portion 460 of the sockets 446a, 446b has a diameter somewhat less than the spherical-shaped end portion 427 of the support rod 426 to aid in retaining the support rods 426 in axial engagement with the end member 424.

Once the spherical-shaped end portion 427 of the support rod 426 is positioned within the spherical-shaped recessed portion 462 of the socket 446a, 446b and the support rod 426 is arranged at the appropriate angle $\alpha_1$ relative to the end member 424, a set screw 428 is threadingly advanced through the threaded aperture 452 and into engagement with the spherical-shaped end portion 427 to lock the support rod 426 in a select angular orientation relative to the end member 424. Engagement of the set screw 428 against the spherical-shaped end portion 427 in turn urges the spherical-shaped end portion 427 into engagement with the ridges or teeth 464 formed along the spherical-shaped recessed portion 462 of the socket 446a, 446b, thereby enhancing engagement of the support rod 426 with the end member 424 to further resistance relative pivotal movement therebetween.

In one embodiment of the invention, the set screws 428 is of the break-off type, including a threaded shank portion 470 adapted for engagement within the threaded aperture 452, and a head portion 472 extending from the threaded shank portion 470 and adapted for engagement by the distal end portion of a driving tool (not shown). In one embodiment, the head portion 472 is selectively removable from the threaded portion 470. In a specific embodiment, the head portion 472 is attached to the threaded portion 470 via a frangible region or fracture initiator 474 adapted to allow the head portion 472 to be snapped off or broken away from the threaded portion 470 once properly engaged against the spherical end portion 427 of the support rod 426. In a further embodiment of the invention, the distal end of the threaded portion 470 defines a number of projections or protrusions 476, such as, for example, a ring-like ridge and/or a series of teeth or spikes that are configured to enhance engagement of the set screw 428 with the spherical end portion 427 of the support rod 426 to provide additionally resistance to relative pivotal movement between the end member 424 and the support rod 426.

Referring to FIGS. 17-19, shown therein is a cage assembly 500 according to yet another form of the present invention. The cage assembly 500 is generally comprised of a first end member 522, a second end member 524, and one or more elongate support members or rods 526 coupled between the first and second end members 522, 524. As will be discussed below, the cage assembly 500 is configured to allow the support rods 526 to pivot relative to at least one of the end members 522, 524, and includes a number of fasteners, such as, for example, set screws 528 (FIG. 19) adapted to lock the support rods 526 at a select angular orientation relative to the end members 522, 524. Although the cage assembly 500 has been illustrated as including a pair of support rods 526, it should be understood that any number of support rods may be used, including a single support rod or three or more support rods.

The support rods 526 are configured similar to the support rods 426 illustrated and described above with regard to the cage assembly 400. However, instead of defining a spherical-shaped end portion, the support rods 526 define a cylindrical-shaped end portion 527 extending in a direction transverse to the longitudinal axis of the support rod 526 to define a T-bar arrangement, the function of which will be discussed below. Similar to the support rods 426, the end portion of the support rods 526 opposite the transversely extending cylindrical-shaped end portion 527 defines an axially extending cylindrical configuration. It should be understood, however, that in other embodiments of the invention, each end portion of the support rods 526 may define a transversely extending cylindrical-shaped end portion 527.

The end member 522 is configured substantially identical to the end member 422 illustrated and described above with regard to the cage assembly 400, including sockets configured to receive the axially extending cylindrical end portions of the support rods 526 therein. In many regards, the end member 524 is configured similar to the end member 522. For example, the end member 524 has a parametrical configuration extending about an open inner region 530 and defining a lateral passage 532 communicating with the open inner region 530. Additionally, the end member 524 has a base portion 540, a pair of oppositely disposed wings or side portions 542a, 542b, an upper/lower engaging surface 544, a pair of sockets or receptacles 546a, 546b defining lateral openings 548, threaded aperture 552 extending along axes 554a, 554b, and a tool receiving aperture 556. However, unlike the end member 522, the end member 524 is configured to pivotally receive the cylindrical-shaped end portions 527 of the support rods 526 to allow for relative pivotal movement between the support rods 526 and the end member 524, the details of which will follow.

In one embodiment of the invention, the sockets 546a, 546b each include an axially extending cylindrical-shaped portion 560 and a transversely extending cylindrical-shaped recessed portion 562 sized and shaped to receive the cylindrical-shaped end portion 527 of a respective support rod 526 therein. In this manner, the support rods 526 are allowed to pivot relative to the end member 524 in a hinge-like manner about a transverse axis T within a range of angular orientations. In the illustrated embodiment of the invention, the end portion 527 of the support rods 526 and the corresponding socket 546a, 546b of the end member 524 are configured to allow selective angular displacement of the support rods 526 relative to the end member 524 about a single axis. This mono-axial configuration substantially prevents angular displacement of the support rods 526 relative to the end member 524 about any axis other than the transverse axis T. However, it should be appreciated that alternative configurations are also contemplated, including bi-axial configurations wherein the end portions 527 of the support rods 526 and the corresponding sockets 546a, 546b are configured to allow selective angular displacement of the support rods 526 relative to the end member 524 about two axes (e.g., the transverse axis T and an axis arranged substantially perpendicular to and coplanar with the transverse axis T). As discussed above with regard to the cage assembly 400, other multi-axial configurations are also contemplated as falling within the scope of the present invention.

As illustrated in FIG. 19, the support rod 526 is allowed to pivot up to an angle $\alpha_2$ along a single plane (e.g., in a posterior-anterior direction), limited only by engagement of the support rod 526 against a surface 566 defined by the axially-extending cylindrical portion 560 of the sockets 546a, 546b. In one embodiment of the invention, the surface 566 is tapered at an angle approximately equal to the angle $\alpha_2$. In a further embodiment of the invention, at least a portion of the cylindrical-shaped recessed portion 562 of the sockets 546a, 546b defines a number of surface projections or protrusions 564, such as, for example, a series of ridges or teeth and/or spikes, the purpose of which will be discussed below. In one embodiment, the surface projections or protrusions 564 are positioned generally opposite the threaded aperture 552; however, it should be understood that other configurations are also contemplated.

In the illustrated embodiment of the invention, the threaded aperture 552 is configured to receive the cylindrical-shaped end portion 527 of the support rod 526 therethrough such that the end portion 527 may be laterally inserted into the sockets 546a, 546b via a side-loading technique. In a further embodiment of the invention, the cylindrical portion 560 of the sockets 546a, 546b has a diameter somewhat less than the outer cross-section of the end portion 527 to aid in retaining the support rods 526 in axial engagement with the end member 524.

Once the cylindrical-shaped end portion 527 of the support rod 526 is positioned within the cylindrical-shaped recessed portion 562 of the socket 546a, 546b and the support rod 526 is arranged at the appropriate angle $\alpha_2$ relative to the end member 524, a set screw 528 is threadingly advanced through the threaded aperture 552 and into engagement with the end portion 527 to lock the support rod 526 in a select angular orientation relative to the end member 524. Engagement of the set screw 528 against the end portion 527 in turn urges the end portion 527 into engagement with the ridges or teeth 564 formed along the cylindrical-shaped recessed portion 562 of the socket 546a, 546b, thereby enhancing engagement of the support rod 526 with the end member 524 to resistance relative pivotal movement therebetween. The set screw 528 may be configured similar to the break-off type set screw 428 illustrated and described above, or may alternatively take on other configurations. The distal end of the set screw 528 preferably defines a number of projections or protrusions 576, such as, for example, a ring-like ridge and/or a series of teeth or spikes that are configured to enhance engagement of the set screw 528 with the cylindrical-shaped end portion 527 of the support rod 526 to provide additionally resistance to relative pivotal movement between the end member 524 and the support rod 526.

Referring to FIGS. 4 and 5, shown therein is the cage assembly 20 positioned between the upper and lower vertebral bodies $V_U$, $V_L$ to maintain the intervertebral space S following removal of a number of vertebral levels (shown in phantom). In the illustrated embodiment of the invention, the end members 22, 24 and the support members 26 are configured to allow the cage assembly 20 to be assembled in situ within the intervertebral space S. It is also contemplated that the components of the cage assembly 20 may be endoscopically inserted into and assembled within the intervertebral space S in a minimally invasive manner. In another embodiment of the invention, the components of the cage assembly 20 may be assembled into one or more sub-assemblies outside of the intervertebral space S, with final assembly of the cage assembly 20 taking place in situ within the intervertebral space S. In a further embodiment of the invention, the cage assembly 20 may be entirely pre-assembled outside of the patient's body prior to insertion within the intervertebral space S.

As will be discussed in greater detail below, in a preferred embodiment of the invention, the entire cage assembly 20 or the individual components of the cage assembly 20 are inserted into the intervertebral space S via a posterior surgical approach. However, it should be understood that the cage assembly 20 or the individual components of the cage assembly 20 may be inserted into the intervertebral space S via other surgical approaches, such as, for example, an anterior approach or a lateral approach. Following the insertion/assembly of the cage assembly 20 within the intervertebral space S, the open inner regions 30 of the end members 22, 24 are preferably positioned generally along the sagittal plane P, with the lateral passages 32 and the open inner region 30 generally facing a posterior direction.

As illustrated in FIG. 4, the engaging surfaces 44 of the end members 22, 24 are positioned against the endplates of the upper and lower vertebral bodies $V_U$, $V_L$, with the support members 26 extending between the end members 22, 24 to maintain a desired height of the intervertebral space S. As illustrated in FIG. 5, the outer peripheral portion of the end member 24 (as well as the end member 22) is preferably positioned generally above the inner edge of the cortical rim R of the vertebral body. In this manner, at least a portion of the end members 22, 24 is engaged against the relatively hard cortical portion of the vertebral endplates, thereby minimizing the likelihood of subsidence of the cage assembly 20 into the relatively soft cancellous portion of the upper and lower vertebral bodies $V_U$, $V_L$. Additionally, the open inner region 30 defined by each of the end member 22, 24 provides significant exposure of the vertebral endplates to enhance bony fusion between the upper and lower vertebral bodies $V_U$, $V_L$.

As discussed above, the support rods 26 may be inserted through the lateral passages 48 of the end members 22, 24 and into the sockets 46a, 46b via a side-loading technique. This technique may be particularly advantageous when assembling the cage assembly 20 in situ within the intervertebral space S. However, as also discussed above, in other embodiments of the invention, the support rods 26 may be pre-assembled with the end members 22, 24 prior to insertion into the intervertebral space S. Once the support rods 26 are engaged within the sockets 46a, 46b, the set screws 28 are tightened into engagement against the end portions of the support rods 26. The set screws 28 function to secure the support rods 26 to the end members 22, 24, thereby fixing the overall height h of the cage assembly 20 to maintain the desired height of the intervertebral space S.

In certain embodiments of the invention, it may be desirable to provide a number of stabilizer members, such as, for example, various types of cross braces or cross support members extending between the support rods 26, to enhance the rigidity and/or structural integrity of the cage assembly 20. In a further embodiment of the invention, as illustrated in FIG. 4, the cage assembly 20 may include a number of elongate rods or posts 29 (shown in phantom). The elongate posts 29 are coupled to the end members 22, 24 and extend outside of the intervertebral space S. In one embodiment of the invention, the elongate posts 29 extend from the set screws 28, and in a further embodiment are formed integral with the set screws 28 to define a unitary, single-piece structure. The elongate posts 29 provide a means for coupling various components to the cage assembly 20 at a location outside of the intervertebral space S. As should be appreciated, various types and configurations of spinal stabilization systems, such as, for example, plate or rod type systems, may be operably attached to the elongate posts 29 to provide additional stability and structural integrity to the cage assembly 20 and/or to provide additional stabilization and support to the portion of the spinal column being treated.

Figure 6B:
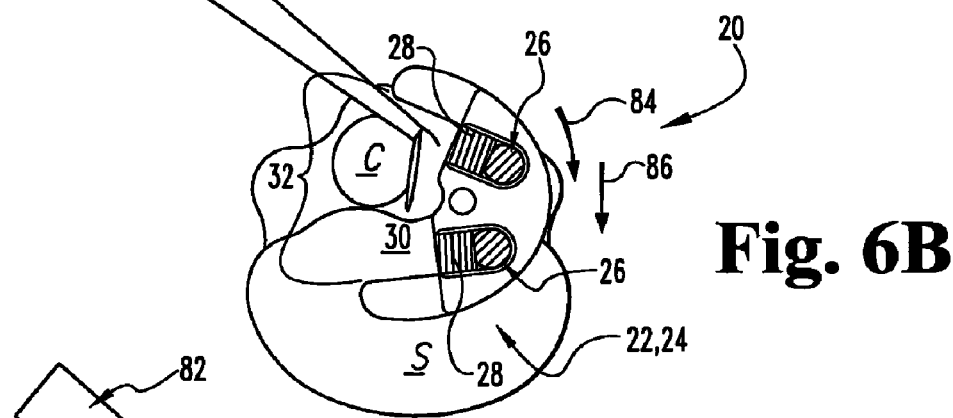
Figure 6C:
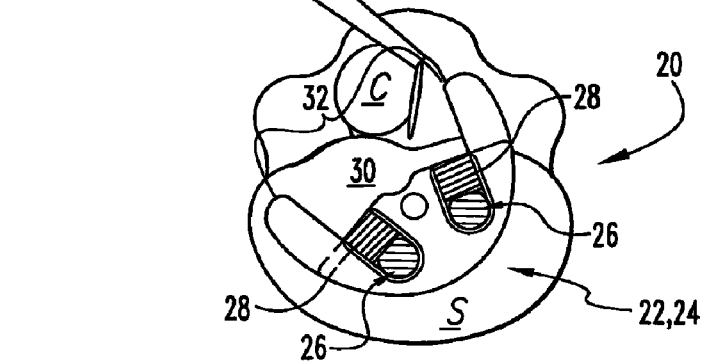

As discussed above, the entire cage assembly 20 or the individual components of the cage assembly 20 may be inserted into the intervertebral space S via a posterior surgical approach. Referring to FIGS. 6A-6C, illustrated therein is a posterior insertion technique according to one embodiment of the present invention. The parametrical configuration of the end members 22, 24 facilitates advancement of the end members 22, 24 and/or the entire cage assembly 20 around the spinal cord C and into the intervertebral space S in such a manner as to minimize retraction and/or manipulation of the spinal cord C and other neural structures.

As illustrated in FIG. 6A, in one embodiment of the invention, the spinal cord C may be slightly retracted in a lateral direction in the direction of arrow 80 via a retractor instrument 82. However, it should be understood that in other embodiments of the invention, the spinal cord C need not necessarily be retracted to accommodate insertion of the cage assembly 20 into the intervertebral space S. The cage assembly 20, with the open inner regions 30 and lateral passages 32 of the end members 22, 24 initially facing the spinal cord C, is rotated or wrapped about the spinal cord C in the direction of arrow 84 while simultaneously being slightly displaced in the direction of arrow 86. In this manner, the distal end portions of the end members 22, 24 are displaced about the spinal cord C along an arc-shaped displacement path. As illustrated in FIGS. 6B and 6C, as the cage assembly 20 is rotated about the spinal cord C, at least a portion of the spinal cord C is introduced through the lateral passage 32 and into the open inner region 30 of the cage assembly 20. Further rotation of the cage assembly 20 in the direction of arrow 84 and simultaneous displacement in the direction of arrow 86 ultimately positions the cage assembly 20 in the position and orientation illustrated in FIG. 5, with the open inner region 30 of the cage assembly 20 positioned generally along the sagittal plane P and with the lateral passages 32 and the open inner region 30 generally facing a posterior direction.

In a further aspect of the present invention, as illustrated in FIGS. 7-10, various types and configurations of fusion devices and/or bone growth promoting materials may be introduced within the intervertebral space adjacent the cage assembly to facilitate or promote bony fusion between the upper and lower vertebral bodies $V_U$, $V_L$.

Referring specifically to FIG. 7, shown therein is a fibular strut 190 disposed between the upper and lower vertebral bodies $V_U$, $V_L$ adjacent the cage assembly 100. The fibular strut 190 has opposite end portions that are positioned within the open inner regions 130 of each of the end members 122, 124, and are preferably positioned in intimate engagement with the vertebral endplates of the upper and lower vertebral bodies $V_U$, $V_L$.

Referring to FIG. 8, shown therein is a fusion cage 192 disposed between the upper and lower vertebral bodies $V_U$, $V_L$ adjacent the cage assembly 100. In the illustrated embodiment, the fusion cage 192 has a cylindrical-shaped configuration and is formed of mesh material. However, it should be understood that other types, shapes and configurations of fusion cages are also contemplated for use in association with the present invention. Similar to the fibular strut 190, the mesh fusion cage 192 has opposite end portions that are positioned within the open inner regions 130 of each of the end members 122, 124, and are preferably positioned in intimate engagement with the vertebral endplates. The mesh fusion cage 192 may be filled with various types of bone growth materials to promote bony fusion between the upper and lower vertebral bodies $V_U$, $V_L$, the details of which would be apparent to one of skill in the art. It should be understood that other types of cages or devices for containing bone growth materials are also contemplated as falling within the scope of the present invention.

Referring to FIGS. 9 and 10, shown therein is a bone growth material 290 disposed between the upper and lower vertebral bodies $V_U$, $V_L$ adjacent the cage assembly 200. The material 290 is contained within the intervertebral space S via a resorbable film or membrane 292. In one embodiment, the resorbable film 292 is comprised of an inner film portion 292a extending about the inner perimeter of the cage assembly 200, and an outer film portion 292b positioned across the open posterior side of the cage assembly 200 to fully contain the bone growth material 290 therein. It should be understood that the inner portion 292a of the resorbable film 292 may extend entirely about the bone growth material 290 to fully encase the material 290. It should also be understood that the resorbable film 292 may extend about the outer perimeter of the cage assembly 200 to contain the bone growth material 290 within the intervertebral space S. Other types of devices and materials for containing the bone growth material 290 are also contemplated for use in association with the present invention, including the use of non-resorbable materials.

It should be understood that various types of bone growth materials and forms thereof may be used in association with the fusion members illustrated in FIGS. 7-10. Such bone growth materials may include, for example, bone graft, bone morphogenetic protein (BMP), allograft, various types of cement, transforming growth factor β1, insulin-like growth factor 1, platelet-derived growth factor, fibroblast growth factor, and LIM mineralization protein. In a further embodiment, the bone growth promoting materials may be provided in a carrier, such as, for example, a sponge, a block, folded sheets, putty and/or paste.

As discussed above, various shapes and configurations of end members and the use of any number of support rods to interconnect the end members are contemplated as falling within the scope of the present invention. For example, as shown in FIGS. 7 and 8, the cage assembly 100 includes a first end member 122, a second end member 124, and three elongate support rods 126 coupled between the first and second end members 122, 124 and engaged thereto via a number of fasteners or set screws 128. The support rods 126 are preferably spaced about the end members 122, 124 and the open inner region 130 in a generally uniform manner. Although the shape and configuration of the end members 122, 124 are somewhat different than that of the end members 22, 24, it should be understood that the purpose and function of the end members 122, 124 are virtually identical to that of the end members 22, 24 illustrated and described above. Likewise, although the cage assembly 200 illustrated in FIGS. 9 and 10 has a somewhat different configuration than that of the cage assembly 20, the purpose and function of the cage assemblies 20, 200 are virtually identical. The cage assembly 200 includes a first end member 222, a second end member 224, and two elongate support rods 226 coupled between the first and second end members 222, 224 and engaged thereto via a number of fasteners or set screws 228. Notably, the anterior portions of the end members 222, 224 are somewhat less prominent than the anterior portions of the end members 22, 24, thereby providing for a slightly larger open inner region 230 which in turn provides for a slightly greater exposure of the vertebral endplates.

Referring to FIGS. 11 and 12, shown therein is a distractor instrument 300 according to one embodiment of the present invention. The distractor 300 extends along a longitudinal axis L and is generally comprised of a first distractor arm 302 and a second distractor arm 304. The first and second distractor arms 302, 304 are coupled to one another via a hinge mechanism or pivot pin 306 which provides for pivotal movement between the distractor arms 302, 304 about a pivot axis 308. As should be appreciated, an inward compression force exerted onto the proximal portions 302a, 304a of the distractor arms in the direction of arrows A will cause the distal end portions 302b, 304b to be outwardly displaced in the direction of arrows B.

In one embodiment, the distractor 300 is provided with a gauge or stop member 310 that is adapted to limit outward displacement of the distal end portion 302b, 304b, which in turn correspondingly limits that amount of distraction provided by the distractor arms 302, 304. In the illustrated embodiment of the distractor 300, the gauge member 310 is configured as a threaded rod having a first end portion 310a engagable with the proximal end portion 304a of the distractor arm 304, and a second end portion 310b engaged within an opening or slot 312 extending through the proximal end portion 302a of the distractor arm 302. As should be appreciated, the position of rod 310 may be adjusted relative to the distractor arm 302 (e.g., by threading the rod 310 into or out of the opening 312) to corresponding control the maximum amount of distraction provided by the distractor arms 302, 304. In this manner, over distraction of the intervertebral space S is avoided.

As shown in FIG. 12, the distal end portions 302b, 304b of the distractor arms 302, 304 preferably define a lateral offset relative to the longitudinal axis L, the purpose of which will be discussed below. In one embodiment of the invention, the distal end portions 302b, 304b have an arcuate-shaped configuration defining the lateral offset. However, other shapes and configurations of the distal end portions 302b, 304b are also contemplated. Additionally, the distal end portions 302b, 304b each preferably define an outwardly extending projection 320 sized and shaped to be received within the tool receiving aperture 56 formed in each of the end member 22, 24. In one embodiment, the projections 320 have a hemispherical configuration; however, other shapes and configurations are also contemplated.

Figure 13A:
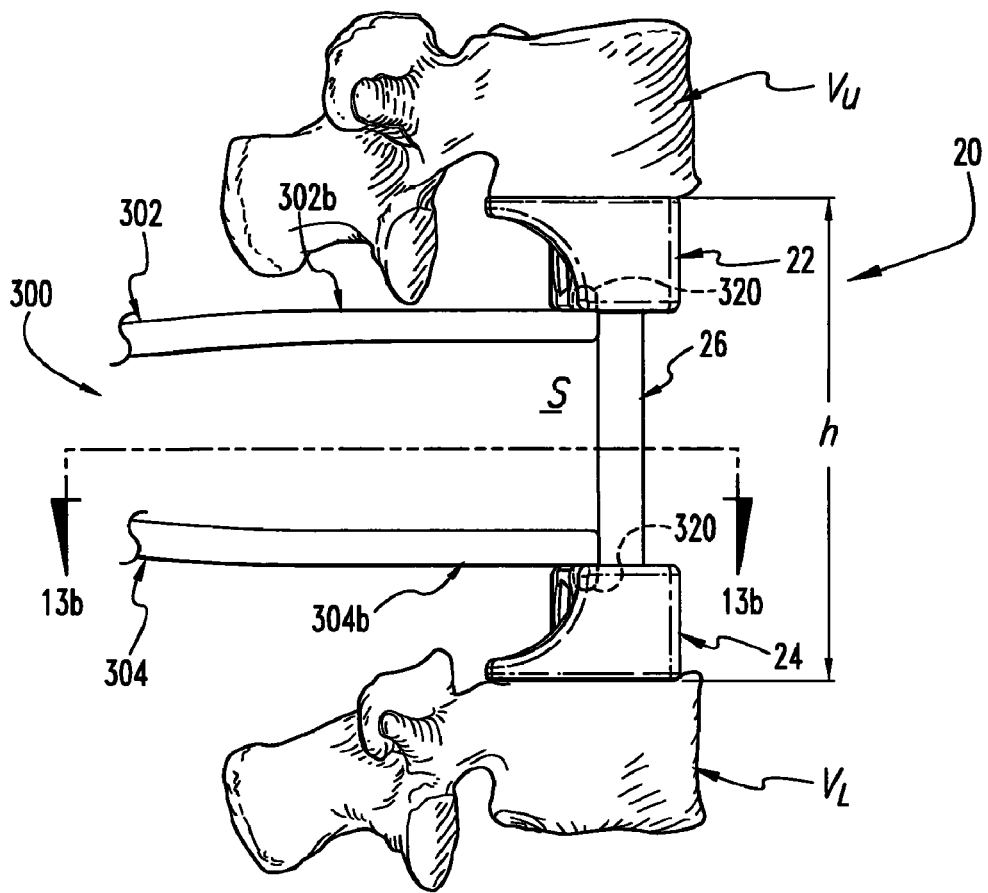
FIG. 13a is a side elevational view of the distal end portions of the distractor instrument illustrated in FIG. 11, as engaged with the upper and lower end members of the cage assembly illustrated in FIG. 1 to distract the upper and lower vertebral bodies.
Figure 13B:
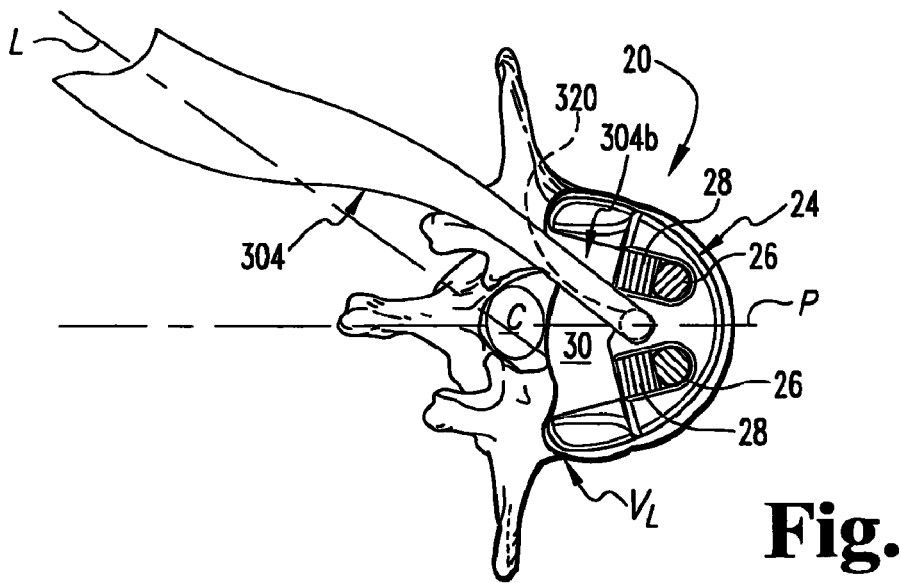

Referring to FIGS. 13a and 13b, the distractor arms 302, 304 are engagable with the end members 22, 24, respectively, via insertion of the projections 320 within the tool receiving apertures 56. As discussed above, the components of the cage assembly 20 are preferably inserted into the intervertebral space S via a posterior surgical approach. Accordingly, the distractor 300 is likewise preferably inserted into the intervertebral space S via a posterior surgical approach. In one embodiment of the invention, the longitudinal axis L of the distractor 300 is generally aligned with the patient's spinal cord C when the distractor arms 302, 304 are properly engaged with the end members 22, 24. Notably, the lateral offset defined by the distal end portions 302b, 304b of the distractor arms 302, 304 provide the distractor 300 with the ability to wrap or extend around the spinal cord C to minimize manipulation and retraction of the spinal cord C while still maintaining secure and stable engagement with the end members 22, 24. In this manner, the risk of injury or trauma to the spinal cord C and other neural structures is reduced.

As an inward compression force is exerted onto the proximal portions 302a, 304a of the distractor arms 302, 304, the distal end portions 302b, 304b are outwardly displaced or spread apart, which in turn urges the end members 22, 24 against the opposing vertebral endplates to distract the upper and lower vertebral bodies $V_U$, $V_L$ to a desired distraction height. Once a desired distraction height is attained, the set screws 28 are tightened into engagement with the support rods 26 to fix the overall height h of the cage assembly 20 and to maintain the desired distraction height of the intervertebral space S. A fusion device and/or a bone growth material may then be inserted into the intervertebral space S adjacent the cage assembly 20. As discussed above, various types of fusion devices or materials may be used to facilitate or promote bony fusion between the upper and lower vertebral bodies $V_U$, $V_L$ including, for example, the fibular strut 190, the fusion cage 192, or the bone growth material 290 contained within the intervertebral space S via the resorbable film 292.

In one embodiment of the invention, the support rods 26 are preloaded into the sockets 46a, 46b of the end members 22, 24 prior to distraction of the intervertebral space S, with the end portions of the support rods 26 extending through the axial thru-openings 50 associated with at least one of the end members 22, 24. In this manner, during distraction, at least one of the end members 22, 24 is slidably displaced along the support rods 26 until the desired distraction height is attained, followed by tightening of the set screws 28 to fix the overall height h of the cage assembly 20. In another embodiment of the invention, the end members 22, 24 may be inserted into the intervertebral space S and spread apart until the desired distraction height is attained, followed by insertion of the support rods 26 into the sockets 46a, 46b and tightening of the set screws 28 to fix the overall height h of the cage assembly 20.

Based upon the foregoing description and illustrations, it should now be appreciated that the cage assemblies 20, 100, 200, 400 and 500 of the present invention enable complete vertebral reconstruction following a vertebrectomy, preferably via a posterior surgical approach. During implantation, the components of the cage assemblies extend or wrap about the spinal cord C and emerging nerve roots to minimize the risk of injury to these neural structures. Additionally, the upper and lower end members of the cage assemblies are engaged against the cortical rim or apophyseal ring of the vertebral endplates, thereby reducing the likelihood of subsidence into the upper and lower vertebrae. Moreover, the cage assemblies of the present invention also provide substantial exposure of the vertebral endplates to promote fusion between the upper and lower vertebral bodies. Furthermore, the cage assemblies provide for relatively uninhibited postoperative follow up with regard to verification of proper fusion/bone growth between the upper and lower vertebral bodies.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An apparatus for supporting vertebral bodies, comprising:
    a first end member adapted to engage a lower endplate of a first vertebral body;
    a second end member adapted to engage an upper endplate of a second vertebral body;
    wherein each of said first and second end members has a perimetrical configuration extending about an open inner region and defining a lateral passage communicating with said open inner region; and
    at least one elongate support member coupled between said first and second end members to maintain an axial space between the first and second vertebral bodies, further comprising a plurality of said elongate support members coupled between said first and second end members; and
    wherein at least one of said first and second end members includes at least one socket sized to receive a corresponding end portion of said at least one elongate support member therein, said at least one socket and said corresponding end portion of said elongate support member configured to allow pivotal movement of said elongate support member relative to said at least one of said first and second end members about at least one axis to correspondingly arrange said first and second end members at variable angular orientations relative to one another.

2. The apparatus of claim 1, wherein said at least one elongate support member extends generally along a longitudinal axis; and
    wherein said at least one socket and said corresponding end portion of said at least one elongate support member are configured to allow pivotal movement of said at least one elongate support member relative to said at least one of said first and second end members about multiple transverse axes arranged transverse to said longitudinal axis.

3. The apparatus of claim 1, wherein said at least one elongate support member extends generally along a longitudinal axis; and
    wherein said at least one socket and said corresponding end portion of said at least one elongate support member are configured to allow pivotal movement of said at least one elongate support member relative to said at least one of said first and second end members about a single transverse axis arranged transverse to said longitudinal axis.

4. The apparatus of claim 1, wherein said at least one socket comprises a spherical-shaped recess, said corresponding end portion of said at least one elongate support member comprising a spherical-shaped end portion disposed within said spherical-shaped recess to allow said pivotal movement about multiple transverse axes.

5. The apparatus of claim 1, wherein said at least one socket comprises a cylindrical-shaped recess, said corresponding end portion of said at least one elongate support member comprising a cylindrical-shaped end portion disposed within said cylindrical-shaped recess to allow said pivotal movement about a single transverse axis.

6. The apparatus of claim 5, wherein said at least one elongate support member extends generally along a longitudinal axis, said cylindrical-shaped end portion extending generally along said single transverse axis.

7. The apparatus of claim 1, wherein each of said first and second end members is U-shaped.

8. The apparatus of claim 1, wherein each of said first and second end members has an outer profile substantially complementary to a cortical rim of the first and second vertebral bodies.

9. The apparatus of claim 1, wherein each of said first and second end members includes at least one socket sized to receive a corresponding end portion of said at least one elongate support member therein.

10. The apparatus of claim 9, wherein each of said first and second end members includes at least one laterally-extending aperture in communication with said at least one socket; and
    further comprising fasteners positioned within respective ones of each of said laterally-extending apertures and engaging said corresponding end portion of said at least one elongate support member to connect said first and second end members to said at least one elongate support member and to correspondingly lock said first and second end members at a select angular orientation relative to one another.

11. The apparatus of claim 9, wherein each of said sockets defined by said first and second end members includes a lateral opening sized to laterally receive a corresponding end portion of said at least one elongate support member therethrough.

12. The apparatus of claim 1, wherein said plurality of said elongate support members comprises at least two of said elongate support members spaced about said open inner region of said first and second end members.

13. The apparatus of claim 12, wherein said plurality of said elongate support members comprises at least three of said elongate support members spaced uniformly about said open inner region of said first and second end members.

14. An apparatus for supporting vertebral bodies, comprising:
    a first end member adapted to engage a lower endplate of a first vertebral body;
    a second end member adapted to engage an upper endplate of a second vertebral body;

wherein each of said first and second end members has a perimetrical configuration extending about an open inner region and defining a lateral passage communicating with said open inner region; and at least one elongate support member coupled between said first and second end members to maintain an axial space between the first and second vertebral bodies; and wherein at least one of said first and second end members includes at least one socket sized to receive a corresponding end portion of said at least one elongate support member therein, said at least one socket and said corresponding end portion of said elongate support member configured to allow pivotal movement of said elongate support member relative to said at least one of said first and second end members about at least one axis to correspondingly arrange said first and second end members at variable angular orientations relative to one another, wherein said at least one of said first and second end members includes at least one laterally-extending aperture in communication with said at least one socket; and further comprising a fastener positioned within said laterally-extending aperture and engaging said corresponding end portion of said at least one elongate support member to lock said elongate support member at a select angular orientation relative to said at least one of said first and second end members and to correspondingly lock said first and second end members at a select angular orientation relative to one another.

15. The apparatus of claim 14, wherein said at least one socket defines a number of surface protrusions adapted to engage said corresponding end portion of said at least one elongate support member to aid in locking said elongate support member at said select angular orientation relative to said at least one of said first and second end members.

16. An apparatus for supporting vertebral bodies, comprising:

a first end member adapted to engage a lower endplate of a first vertebral body;

a second end member adapted to engage an upper endplate of a second vertebral body;

wherein each of said first and second end members has a perimetrical configuration extending about an open inner region and defining a lateral passage communicating with said open inner region; and at least one elongate support member coupled between said first and second end members to maintain an axial space between the first and second vertebral bodies; and wherein at least one of said first and second end members includes at least one socket sized to receive a corresponding end portion of said at least one elongate support member therein, said at least one socket and said corresponding end portion of said elongate support member configured to allow pivotal movement of said elongate support member relative to said at least one of said first and second end members about at least one axis to correspondingly arrange said first and second end members at variable angular orientations relative to one another, and wherein said at least one socket includes a lateral opening sized to laterally receive said corresponding end portion of said at least one elongate support member therethrough.

17. An apparatus for supporting vertebral bodies, comprising:

a first end member adapted to engage a lower endplate of a first vertebral body;

a second end member adapted to engage an upper endplate of a second vertebral body;

wherein each of said first and second end members has a perimetrical configuration extending about an open inner region and defining a lateral passage communicating with said open inner region; and a plurality of elongate support member coupled between said first and second end members to maintain an axial space between the first and second vertebral bodies; and wherein at least one of said first and second end members includes at least one socket sized to receive a corresponding end portion of a respective one of said plurality of elongate support members therein, said at least one socket including a lateral opening sized to laterally receive said corresponding end portion of said respective elongate support member therethrough, said at least one socket and said corresponding end portion of said respective elongate support member configured to allow pivotal movement of said respective elongate support member relative to said at least one of said first and second end members about at least one axis to correspondingly arrange said first and second end members at variable angular orientations relative to one another.

18. The apparatus of claim 17, wherein said at least one socket comprises a spherical-shaped recess, said corresponding end portion of said respective elongate support member comprising a spherical-shaped end portion disposed within said spherical-shaped recess to allow said pivotal movement about multiple axes.

19. The apparatus of claim 17, wherein said at least one socket comprises a cylindrical-shaped recess, said corresponding end portion of said respective elongate support member comprising a cylindrical-shaped end portion disposed within said cylindrical-shaped recess to allow said pivotal movement about a single transverse axis.

20. An apparatus for supporting vertebral bodies, comprising:

a first horseshoe-shaped member adapted to engage a first vertebral body;

a second horseshoe-shaped member adapted to engage a second vertebral body; and at least one elongate support member coupled between said first and second horseshoe-shaped members to maintain an axial space between the first and second vertebral bodies, further comprising a plurality of said elongate support members coupled between said first and second horseshoe-shaped members; and wherein at least one of said first and second horseshoe-shaped members includes at least one socket sized to receive a corresponding end portion of said at least one elongate support member therein, said at least one socket and said corresponding end portion of said elongate support member configured to allow pivotal movement of said elongate support member relative to said at least one of said first and second horseshoe-shaped members about at least one axis to correspondingly arrange said first and second horseshoe-shaped members at variable angular orientations relative to one another.

21. The apparatus of claim 20, wherein each of said first and second horseshoe-shaped members has a perimetrical configuration extending about an open inner region and a lateral passage in communication with said open inner region.

22. The apparatus of claim 20, wherein each of said first and second horseshoe-shaped members has an outer profile substantially complementary to an apophyseal ring of the first and second vertebral bodies.

23. The apparatus of claim 20, wherein each of said first and second horseshoe-shaped members has a semi-circular configuration.

24. The apparatus of claim 20, wherein said at least one socket comprises a spherical-shaped recess, said corresponding end portion of said at least one elongate support member comprising a spherical-shaped end portion disposed within said spherical-shaped recess to allow said pivotal movement about multiple axes.

25. The apparatus of claim 20, wherein said at least one socket comprises a cylindrical-shaped recess, said corresponding end portion of said at least one elongate support member comprising a cylindrical-shaped end portion disposed within said cylindrical-shaped recess to allow said pivotal movement about a single transverse axis.

26. The apparatus of claim 25, wherein said at least one elongate support member extends generally along a longitudinal axis, said cylindrical-shaped end portion extending generally along said single transverse axis.

27. The apparatus of claim 20, wherein said at least one of said first and second end members includes at least one laterally-extending aperture in communication with said at least one socket; and
further comprising a fastener positioned within said laterally-extending aperture and engaging said corresponding end portion of said at least one elongate support member to lock said at least one elongate support member at a select angular orientation relative to said at least one of said first and second horseshoe-shaped members and to correspondingly lock said first and second horseshoe-shaped members at a select angular orientation relative to one another.

28. The apparatus of claim 20, wherein said plurality of said elongate support members comprises two of said elongate support members spaced about said open inner region of said first and second horseshoe-shaped members.

29. The apparatus of claim 28, wherein said plurality of said elongate support members comprises at least three of said elongate support members spaced uniformly about said open inner region of said first and second horseshoe-shaped members.

30. An apparatus for supporting vertebral bodies, comprising:
a first horseshoe-shaped member adapted to engage a first vertebral body;
a second horseshoe-shaped member adapted to engage a second vertebral body; and
at least one elongate support member coupled between said first and second horseshoe-shaped members to maintain an axial space between the first and second vertebral bodies; and
wherein at least one of said first and second horseshoe-shaped members includes at least one socket sized to receive a corresponding end portion of said at least one elongate support member therein, said at least one socket and said corresponding end portion of said elongate support member configured to allow pivotal movement of said elongate support member relative to said at least one of said first and second horseshoe-shaped members about at least one axis to correspondingly arrange said first and second horseshoe-shaped members at variable angular orientations relative to one another, and wherein said at least one socket includes a lateral opening sized to laterally receive said corresponding end portion of said at least one elongate support member therethrough.

* * * * *